(12) United States Patent
Mizutani et al.

(10) Patent No.: US 6,761,955 B2
(45) Date of Patent: *Jul. 13, 2004

(54) ABSORBENT ARTICLE (75) Inventors: Satoshi Mizutani, Kagawa (JP);
Makoto Suekane, Kagawa (JP);
Etsuko Tagami, Kagawa (JP); Kazuya Nishitani, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 267 days.

This patent is subject to a terminal disclaimer.

(21) Appl. No.: 09/992,799

(22) Filed: Nov. 14, 2001

(65) Prior Publication Data

US 2002/0064624 A1 May 30, 2002

(30) Foreign Application Priority Data

Nov. 27, 2000 (JP) ........................................ 2000-358760

(51) Int. Cl.$^7$ ............................ B32B 3/04; A61F 13/15; A61F 13/20
(52) U.S. Cl. ............. 428/126; 604/385.04; 604/385.01; 604/385.28; 604/385.23; 604/365; 604/367; 604/370; 604/374; 604/378; 604/384
(58) Field of Search ..................... 428/126; 604/385.04, 604/385.01, 385.28, 385.23, 365, 367, 370, 374, 378, 384

(56) References Cited

U.S. PATENT DOCUMENTS 6,548,731 B2 * 4/2003 Mizutani et al. ............. 604/365

2001/0053899 A1 12/2001 Mizutani et al.

FOREIGN PATENT DOCUMENTS

| EP | 0 391 727 B2 | 10/1990 |
| EP | 0 745 637 A2 | 12/1996 |
| EP | 0 747 029 A1 | 12/1996 |
| EP | 1 133 963 A2 | 9/2001 |
| EP | 1 208 828 A2 | 5/2002 |

OTHER PUBLICATIONS

Australian Patent Office Search Report dated Aug. 21, 2003.

* cited by examiner

*Primary Examiner*—Harold Pyon
*Assistant Examiner*—Catherine A. Simone
(74) *Attorney, Agent, or Firm*—Darby & Darby (57) ABSTRACT

Disclosed is an absorbent article including a topsheet, a backsheet and an absorbent core positioned between the topsheet and the backsheet, and having leakage-preventing side walls on a liquid-receiving side of the article. The leakage-preventing side walls extend in a longitudinal direction of the article and lie opposite one another in a width direction of the article. At least a liquid-receiving face of each leakage-preventing side wall is made of a fibrous sheet that contains hydrophobic fibers thermally bonded to one another and hydrophilic fibers shorter than the hydrophobic fibers. At least a part of the hydrophilic fibers form aggregates which are dispersed in the fibrous sheet and are bonded to the hydrophobic fibers.

9 Claims, 11 Drawing Sheets

ABSORBENT ARTICLE

BACKGROUND OF THE INVENTION

1. Field of the Invention

The present invention relates to an absorbent article capable of absorbing and retaining liquids discharged from the wearer's body such as typically menses and others. More particularly, it relates to an absorbent article capable of reducing a wet feel between the wearer's skin and leakage-preventing side walls of the article so as not to give an unpleasant feel to a wearer.

2. Description of the Related Art

Various absorbent articles such as sanitary napkins, incontinence pads, disposable diapers and others have heretofore been developed and known. These absorbent articles comprise a liquid-impermeable backsheet, a liquid-permeable topsheet, and an absorbent core between the topsheet and backsheet, and have leakage-preventing side walls extending in the longitudinal direction of the article on the two sides of the absorbent core.

The leakage-preventing side walls are made of a non-woven fabric comprising mainly hydrophobic synthetic fibers. In the leakage-preventing side walls made of such a nonwoven fabric of hydrophobic synthetic fibers, the liquid retentiveness of the fibers themselves is low. Accordingly, when kept in contact with a large amount of liquid, the leakage-preventing side walls are highly resistant to liquid permeation, and therefore can prevent the liquid from leaking out of them.

On the other hand, Japanese Unexamined Patent Publication No. 322877/1996 discloses leakage-preventing side walls made of a plastic sheet. The leakage-preventing side walls made of a plastic sheet disclosed are also highly resistant to liquid permeation.

However, in the leakage-preventing side walls made of a nonwoven fabric comprising mainly the hydrophobic synthetic fibers, the liquid retentiveness of the fibers themselves that constitute the nonwoven fabric is low, and the fibers have almost no capillary action. Therefore, a small amount of body fluid or sweat having been once adhered to the surface of the leakage-preventing side walls is difficult to move therefrom. As a result, such a small amount of liquid will often remain between the wearer's skin and the leakage-preventing sidewalls, and therefore gives a wet feel to a wearer.

On the other hand, the leakage-preventing side walls made of a plastic sheet often stick tightly to the wearer's skin, and therefore a small amount of body fluid or sweat is apt to remain between their surface and the wearer's skin. As a result, the surface of the leakage-preventing side walls has a sticky feel and gives an unpleasant feel to a wearer. In addition, the leakage-preventing side walls made of a plastic sheet are poorly pervious to vapor, and they are apt to give a stuffy feel.

SUMMARY OF THE INVENTION

The present invention has been worked out in view of the shortcoming in the prior art set forth above. It is therefore an object of the present invention to provide an absorbent article provided with leakage-preventing side walls which are highly resistant to liquid and have the ability to absorb a small amount of liquid and which hardly give a wet feel to a wearer.

According to the present invention, there is provided an absorbent article comprising a topsheet, a backsheet and an absorbent core positioned between the topsheet and the backsheet, and having leakage-preventing side walls on a liquid-receiving side of the article, the leakage-preventing side walls extending in a longitudinal direction of the article and lying opposite one another in a width direction of the article, wherein at least a liquid-receiving face of each leakage-preventing side wall is made of a fibrous sheet that contains hydrophobic fibers thermally bonded to one another and hydrophilic fibers shorter than the hydrophobic fibers, and at least a part of the hydrophilic fibers form aggregates which are dispersed in the fibrous sheet and are bonded to the hydrophobic fibers.

When the fibrous sheet comprises an outer layer and an inner layer in section with respect to the thickness thereof, it is desirable that the hydrophilic fiber aggregates are not in the outer layer but are only in the inner layer. In this case, if the basis weight of the fibrous sheet falls between 20 and 60 g/m$^2$, and if the basis weight of the outer layer of the fibrous sheet falls between 5 and 15 g/m$^2$, the distance between the liquid-receiving face of the side wall and the hydrophilic fiber aggregates existing in the side wall can be shortened so that the hydrophilic fiber aggregates can readily absorb the moisture having adhered to the outer layer of the fibrous sheet.

The fibrous sheet may have a plurality of apertures formed therein. Preferably, the fibrous sheet is folded back at the top of the side wall. If desired, it may be folded twice or more. A liquid-absorbent layer may be disposed between the confronting faces of the thus-folded fibrous sheet.

Also preferably, the fiber density of the hydrophilic fiber aggregates is higher than the fiber density of a portion of the fibrous sheet not containing the aggregates therein. More preferably, the fiber density of the hydrophilic fiber aggregates falls between 1.5 and 3 times the fiber density of the portion of the fibrous sheet not containing the aggregates therein.

For example, the hydrophobic fibers have a length of from 38 to 64 mm, and the hydrophilic fibers have a length of from 5 to 25 mm. Preferably, the length of the hydrophilic fibers is at most ½ of that of the hydrophobic fibers. If the fiber lengths are within the ranges, the hydrophilic fibers can be readily massed or crimped to form the aggregates and dispersed among the hydrophobic fibers by using a conventional carding unit.

Also preferably, the fibrous sheet contains from 70 to 98% by weight of hydrophobic fibers and from 2 to 30% by weight of hydrophilic fibers. When the amount of the hydrophilic fibers in the fibrous sheet is at most 30% by weight, more preferably at most 10% by weight, the hydrophilic fiber aggregates can be well dispersed in the fibrous sheet while being suitably spaced from each other therein.

In the absorbent article of the invention, the fibrous sheet (e.g., nonwoven fabric) for forming the leakage-preventing side wall comprises mainly the hydrophobic fibers thermally bonded to one another and contains the hydrophilic fibers which are massed or crimped to form the aggregates having a higher density and are dispersed in the fibrous sheet. When a small amount of liquid or sweat is given to the leakage-preventing side walls, it is well retained by the hydrophilic fiber aggregates having a higher density and dispersed therein, owing to their hydrophilic capillary action. Accordingly, the small amount of liquid having been given to the side walls remains little in the space between the hydrophobic fibers therein, and therefore returns little to the wearer's skin. Therefore, the surface of the leakage-preventing side wall can be readily kept dry and hardly gives a wet feel to the wearer's skin.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENTS

Figure 1:
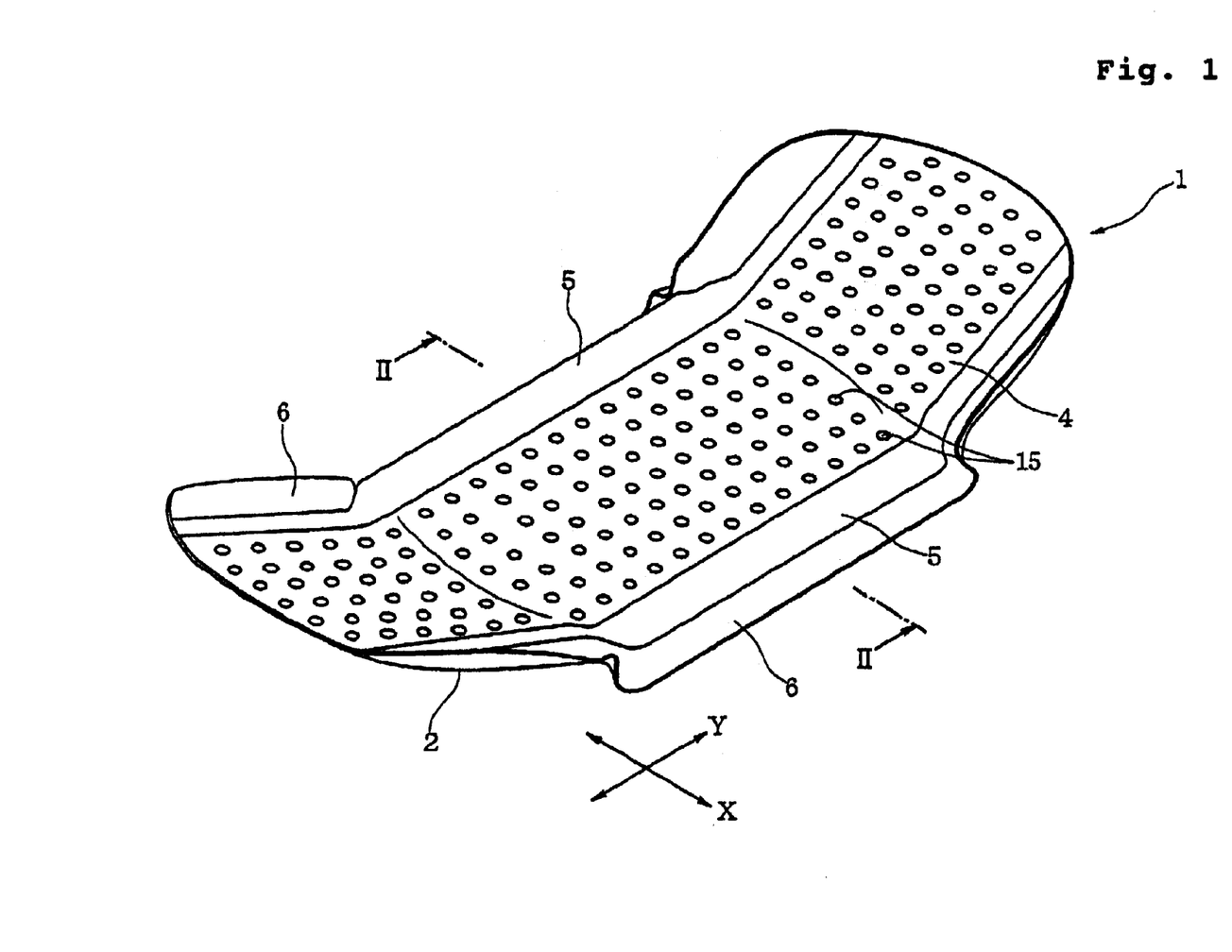
FIG. 1 is a perspective view of a sanitary napkin as one embodiment of the absorbent article of the invention.
Figure 2:
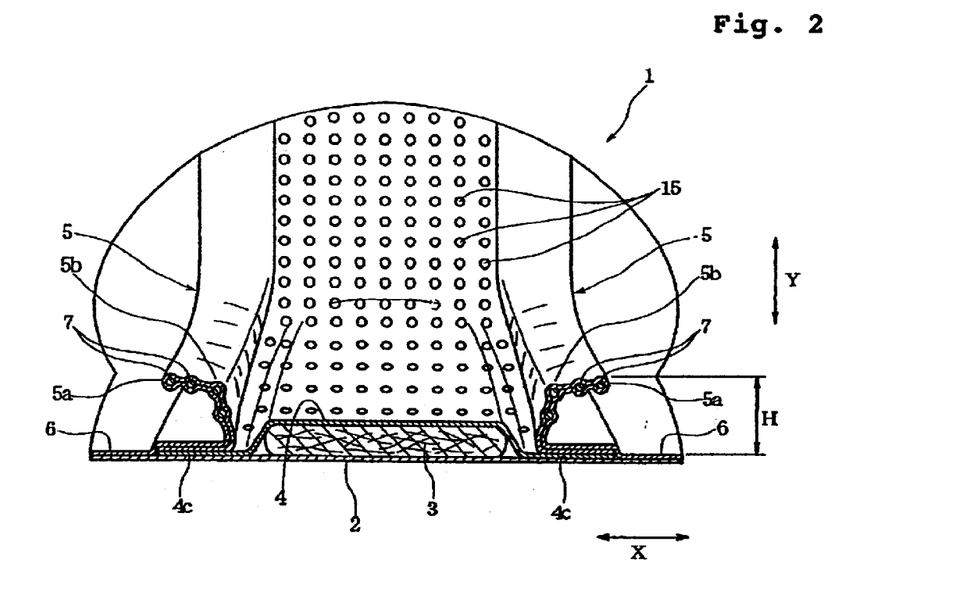
FIG. 2 is a cross-sectional view of the sanitary napkin of FIG. 1, taken along the line II—II.
Figure 3:
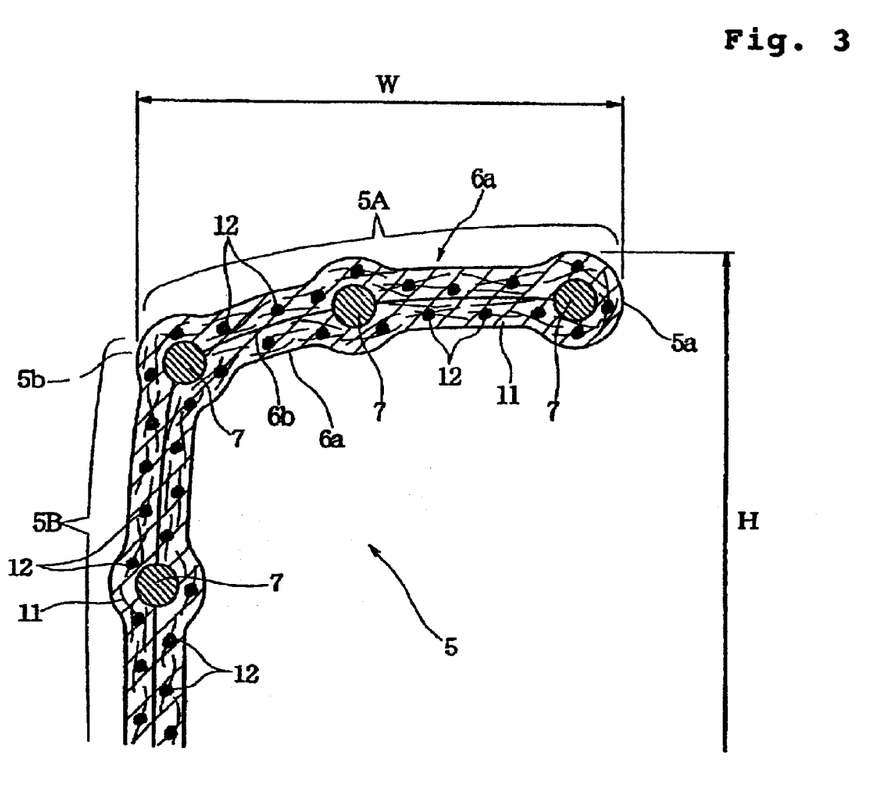
FIG. 3 is an enlarged cross-sectional view of a portion of one embodiment of the leakage-preventing side wall in the absorbent article of the invention.
Figure 9:
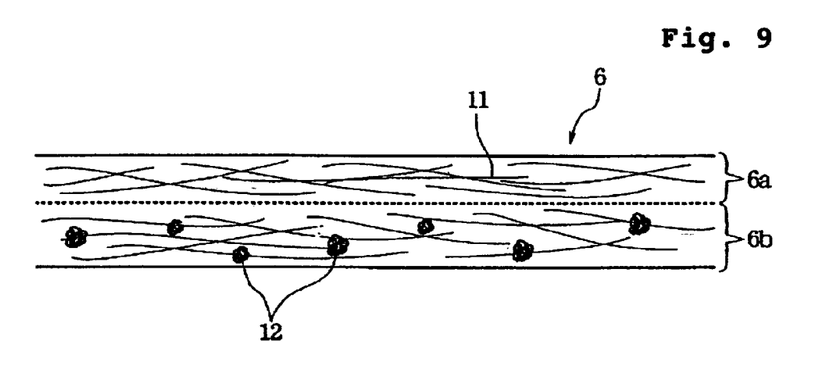
FIG. 9 is an enlarged cross-sectional schematic view of a portion of a nonwoven fabric sheet for use in the invention.
Figure 10:
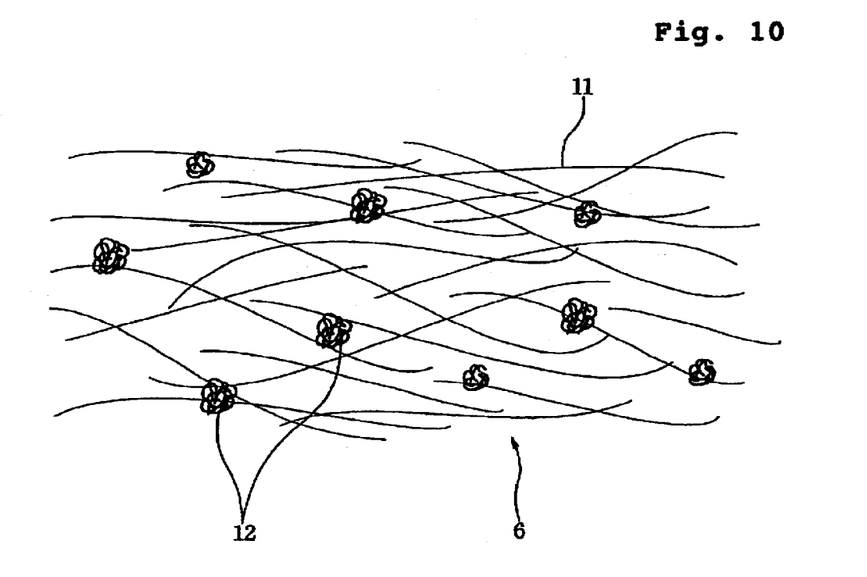
FIG. 10 is a still enlarged view of a portion of the nonwoven fabric sheet of FIG. 9.
Figure 11:
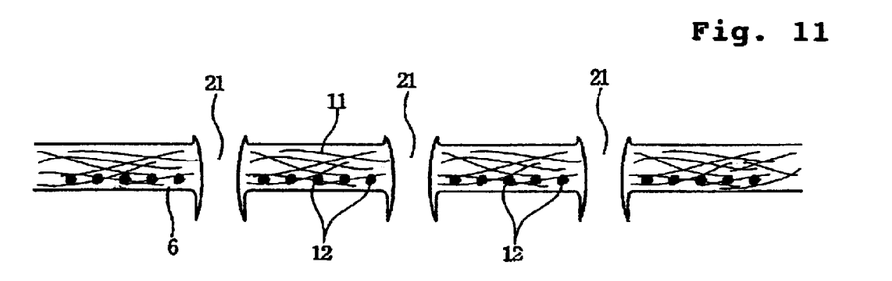
FIG. 11 is a cross-sectional view of a portion of an apertured nonwoven fabric sheet for use in the invention.
Figure 12:
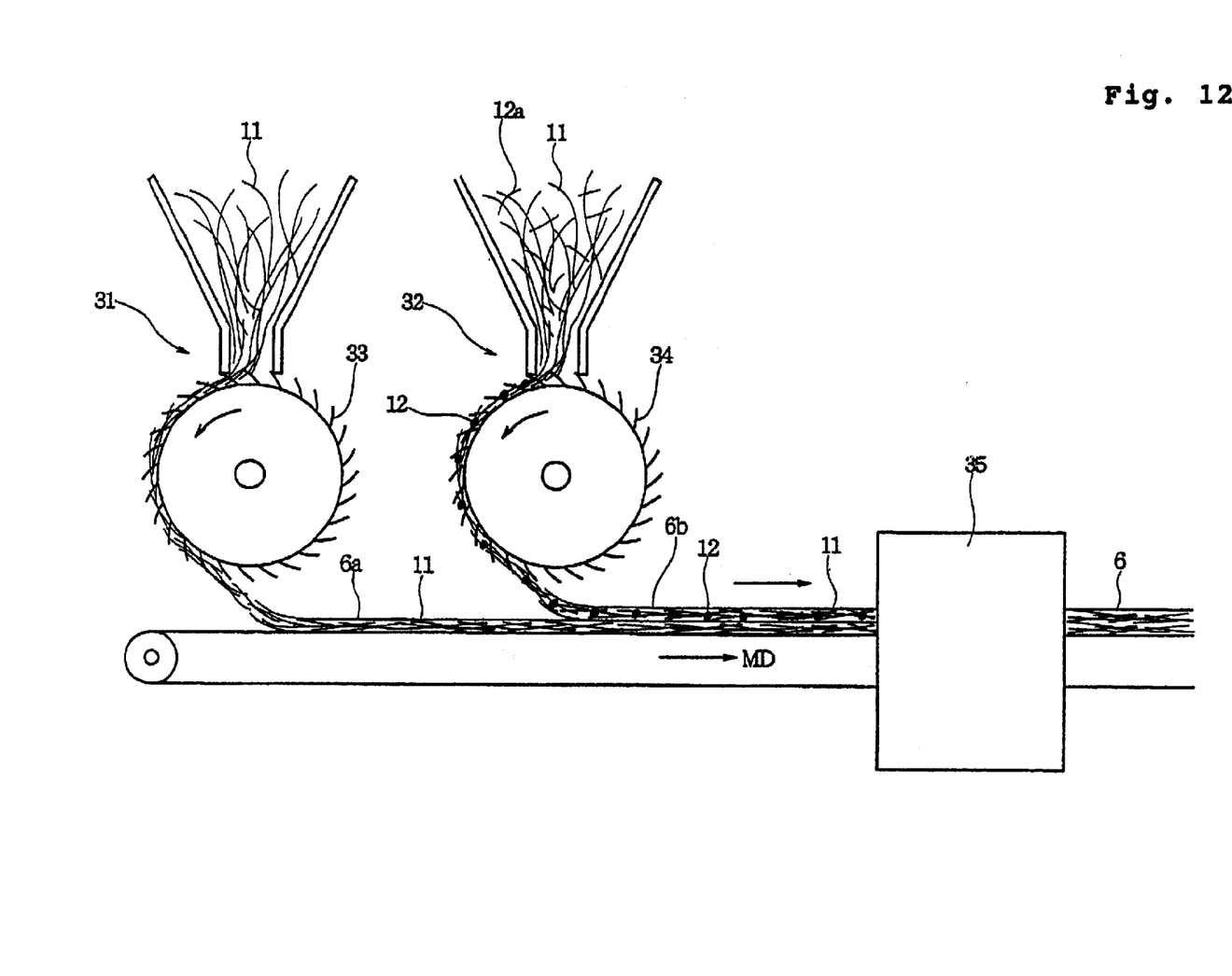
FIG. 12 is an explanatory view showing one example of a method for producing a nonwoven fabric sheet for use in the invention.
Figure 13A:
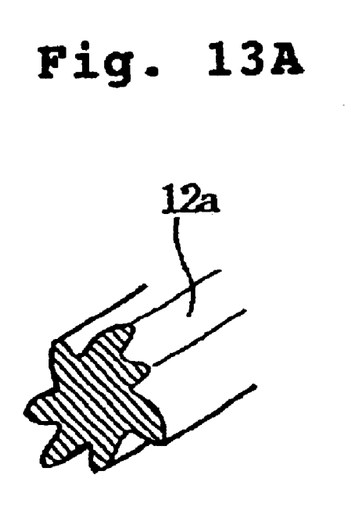
FIG. 13A and FIG. 13B are partially-cut, enlarged perspective views showing preferred cross-sectional profiles of hydrophilic fibers for use in the invention.
Figure 13B:
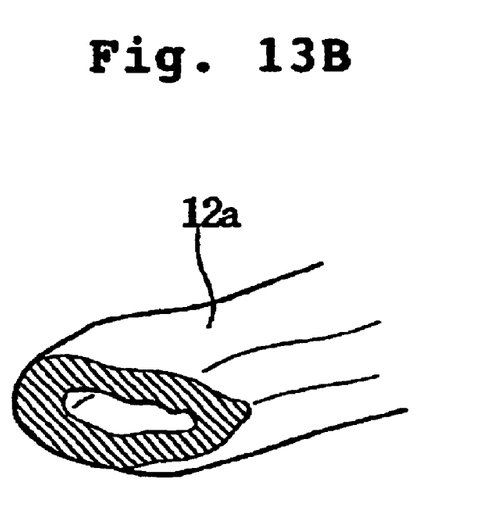

The present invention will be discussed hereinafter in detail in terms of the preferred embodiment of an absorbent article according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention. FIG. 1 is a perspective view of a sanitary napkin 1, as one embodiment of the absorbent article of the invention, in which the liquid-receiving side of the sanitary napkin is in view. FIG. 2 is a cross-sectional view of FIG. 1, taken along the line II—II. FIG. 3 is an enlarged cross-sectional view of a portion of one embodiment of the leakage-preventing side walls of the sanitary napkin. FIG. 4 to FIG. 8 show modifications of the leakage-preventing side walls. FIG. 9 is an enlarged schematic view showing the cross section of a sheet to form the leakage-preventing side walls. FIG. 10 is a still enlarged view of a portion of the sheet of FIG. 9. FIG. 11 is a cross-sectional view of an apertured nonwoven fabric sheet to form the leakage-preventing side walls. FIG. 12 is an explanatory view showing one example of a method for producing a sheet to form the leakage-preventing side walls. FIG. 13A and FIG. 13B show the cross section of some examples of hydrophilic fibers for use in the invention.

The sanitary napkin 1 of FIG. 1 and FIG. 2 comprises a backsheet 2 to be fitted to an external support such as typically an undergarment; an absorbent core 3 which is nearly in the center region, relative to the width direction (X-direction), of the sanitary napkin and which is to absorb liquids such as menses discharged from the wearer's body; and a topsheet 4 to cover the liquid-receiving face of the absorbent core 3. Both side portions 4c of the topsheet 4 lying opposite one another in the width direction (X-direction) are joined to the surface of the backsheet 2 outside of the absorbent core 3.

On both sides of the sanitary napkin 1 lying opposite one another in the width direction (X-direction), formed are a pair of leakage-preventing side walls 5 and 5 that extend in the longitudinal direction (Y-direction). In the embodiment shown, each leakage-preventing side wall 5 is formed from one fibrous sheet (e.g., nonwoven fabric sheet) 6. As shown in FIG. 2, a portion of the nonwoven fabric sheet 6 is folded into two-layer structure. The two-layer portion of the nonwoven fabric sheet 6 is further folded outwardly into four-layer structure. The nonwoven fabric sheet 6 thus folded is joined onto the side portion 4c of the topsheet 4 and onto the backsheet 2 outside of the side portion 4c, except for its portion forming the leakage-preventing side wall 5. In both front and rear end portions in the longitudinal direction (Y-direction) of the sanitary napkin 1, particularly, the nonwoven fabric sheet 6 is secured on the side portion 4c of the topsheet 4 while being kept in the four-layer structure.

Here, joining of the topsheet 4, the backsheet 2 and the nonwoven fabric sheet 6 can be carried out by adhering them with a hot-melt adhesive or by fusing them with a hot embossing roll.

The backsheet 2 is formed from a liquid-impermeable sheet. For this backsheet 2, usable is any of an air-permeable (breathable) resin film, a spun-bonded or spun-laced nonwoven fabric specifically processed for water repellency, and a nonwoven fabric of which the back is laminated with an air-permeable resin film. Preferably, an adhesive layer is disposed on the back of the backsheet 2, via which the sanitary napkin 1 is secured on an external support such as an undergarment; and the adhesive layer is preferably coated with a released paper (or separate paper) that protects it until use of the sanitary napkin 1.

The absorbent core 3 is made of ground pulp or a mixture of ground pulp and a superabsorbent polymer (SAP). Concretely, ground pulp or a mixture of ground pulp and a superabsorbent polymer is wrapped with an absorbent sheet such as tissue paper. For the absorbent core 3, also usable are air-laid pulp, an air-laid nonwoven fabric, a spun-laced nonwoven fabric containing hydrophilic fibers, a stretchable/non-stretchable melt-blown nonwoven fabric treated to be hydrophilic, a fiber aggregate comprising continuous filaments of regenerated cellulose fibers, etc. The above-named materials may also be used as a liquid-absorbent layer to be provided in the leakage-preventing side wall.

The topsheet 4 is a liquid-permeable sheet, and it is formed from, for example, a resin film having a large number of apertures 15 formed therein, a liquid-permeable nonwoven fabric comprising hydrophobic synthetic fibers and hydrophilic fibers, a nonwoven fabric formed from hydrophobic synthetic fibers and having a large number of apertures 15 formed therein. For the topsheet 4, also usable is a sheet which contains hydrophilic fiber aggregates as in the nonwoven fabric sheet 6 for the leakage-preventing side walls 5, 5 and is formed with a large number of apertures 15.

As in FIG. 2 and FIG. 3, each leakage-preventing sidewall 5 is formed from the raised portion of one nonwoven fabric sheet 6. The nonwoven fabric sheet 6 is folded back at the top (free end) 5a of the leakage-preventing side wall 5 so that one surface of the nonwoven fabric sheet 6 is exposed outside of the side wall 5 and the other surface thereof is inside of the side wall 5.

Each leakage-preventing side wall 5 rises from the topsheet 4 and is so curved at the point 5b that the top 5a is directed outward. In this, the portion extending between the top 5a and the curved point 5b and having its surface directed upward is a first portion 5A intended to come into contact with the skin of a wearer; and the portion extending upwardly from the surface of the topsheet 4 to the curved point 5b and having its surface directed toward the center of the sanitary napkin 1 is a second portion 5B. The height, H, of each leakage-preventing side wall 5 from the surface of the sanitary napkin 1 at its side edge preferably falls between 5 and 30 mm; and the width, W, of the first portion 5A preferably falls between 5 and 40 mm.

Inside of the leakage-preventing side wall 5, a plurality of (four in FIG. 2) elastic members 7 are disposed in parallel with one another between the confronting faces of the two-folded nonwoven fabric sheet 6. These elastic members 7 are joined to the nonwoven fabric sheet 6, while being stretched in the longitudinal direction (Y-direction). Therefore, when the sanitary napkin 1 is in a free condition, the longitudinal elastic contractive force of the elastic members 7 acts on the nonwoven fabric sheets 6 forming the leakage-preventing side walls 5.

In both front and rear end portions in the longitudinal direction (Y-direction) of the sanitary napkin 1, as has been described hereinabove, the nonwoven fabric sheet 6 is secured while being kept in the four-layer structure. Owing to the elastic contractive force of the elastic members 7 acting on the leakage-preventing side wall 5, therefore, the sanitary napkin 1 is concavely curved in the longitudinal direction, and, as a result, the leakage-preventing side walls 5 and 5 are to rise toward the skin of a wearer at both sides of the absorbent core 3.

The elastic members 7 are, for example, made of a film, flat yarns or filaments comprising mainly a thermoplastic elastomeric resin such as polyurethane, SEBS, SIS, SEEPS or the like. Alternatively, the elastic members 7 may also be made of filaments comprising mainly a natural rubber. The individual elastic members 7 are, while being stretched under a tensile load (tension) of from 0.294 to 1.47 N to about 1.1 to 2 times the original length, adhered to the nonwoven fabric sheet 6.

As in the schematic views of FIG. 9 and FIG. 10, the nonwoven fabric sheet 6 to form the leakage-preventing side wall 5 comprises hydrophobic synthetic fibers 11 and hydrophilic fiber aggregates 12. The hydrophobic synthetic fibers 11 may have a length of from 38 to 64 mm and a fineness of from 2.2 to 6.6 dtex. Hydrophilic fibers 12a for forming the aggregates 12 may be natural cellulose fibers of, for example, cotton or rayon, and may have a length of from 5 to 25 mm. For the hydrophilic fibers 12a, preferred is cotton.

The fineness of the cotton may fall between 1.2 and 11 dtex or so. Here, it should be noted that some of the hydrophilic fibers 12a may be dispersed among the hydrophobic fibers 11 in the nonwoven fabric sheet 6 without being formed into the aggregates 12. In this case, however, it is preferred that at least a half of the hydrophilic fibers 12a in the nonwoven fabric sheet 6 are formed into the aggregates 12.

The hydrophilic fibers 12a are of natural cellulose, having a modified cross-section profile as in FIG. 13A or a hollow cross-section profile as in FIG. 13B. For example, they are cotton fibers. The modified cross-section fibers are meant to indicate that their surfaces are not smooth as not having a circular or oval cross section, but their surfaces are modified to have grooves or recesses. The hydrophilic fibers having such modified cross-section profiles have a large surface area to increase liquid absorbing and retaining capacity. Natural cellulose fibers having fibril capillaries are also preferred for the hydrophilic fibers 12a for forming the aggregates 12, as they can increase liquid absorbing and retaining capacity.

The shorter hydrophilic fibers 12a are massed or crimped to form aggregates 12. The fiber density of the aggregates 12 is higher than that of the hydrophobic synthetic fibers 11 in the portion not containing the hydrophilic fiber aggregates 12, and than that of the hydrophobic synthetic fibers 11 and hydrophilic fibers 12a not forming aggregates 12 in the portion not containing the hydrophilic fiber aggregates 12 but containing the hydrophilic fibers 12a not forming aggregates 12.

The hydrophilic fiber aggregates 12 are dispersed in a fibrous web forming the nonwoven fabric sheet 6, and are held by the hydrophobic synthetic fibers 11 therein. As used herein, the term "hydrophilic fiber aggregate" refers to hydrophilic fibers which are roundly massed or crimped to be entangled together so as to have a higher fiber density than the fiber density of the portion not containing the aggregates therein.

Detail of such a sheet comprising mainly hydrophobic fibers and having hydrophilic fiber aggregates dispersed therein has been disclosed in commonly owned co-pending U.S. patent application Ser. No. 09/883,970. Disclosure of the above-identified commonly owned co-pending application is herein incorporated by reference.

Preferably, the fiber density of the hydrophilic fiber aggregates 12 falls between 1.5 and 3 times the fiber density of the portion not containing the aggregates 12. For example, the fiber density of the aggregates 12 is 0.03 g/cm$^3$, and the fiber density of the portion not containing the aggregates 12 falls between 0.05 and 0.09 g/cm$^3$.

At least the surface of the hydrophobic synthetic fibers 11 is formed from a low-melting-point material. Preferably, the hydrophobic synthetic fibers 11 are core/sheath-structured bicomponent fibers in which the core is PP (polypropylene) or PET (polyethylene terephthalate) and the sheath is PE (polyethylene). Also preferably, the hydrophobic synthetic fibers 11 contain titanium oxide to be white-opaque. With from 0.5 to 10% by weight of titanium oxide in the hydrophobic synthetic fibers 11, the leakage-preventing side walls 5 can be white, and they can conceal the blood absorbed by the aggregates 12 dispersed in the nonwoven fabric sheet 6 that forms the side walls.

The nonwoven fabric sheet 6 to form the leakage-preventing side wall 5 is a thermal-bonded nonwoven fabric, preferably that produced in a through-air bonding process. In this, the hydrophobic synthetic fibers 11 are thermally fused together, and the hydrophilic fiber aggregates 12 of cotton or the like are secured to the surfaces of the hydrophobic synthetic fibers 11, as the surfaces exhibit fusion bonding force in molten or semi-molten condition.

In order that the hydrophilic fiber aggregates 12 are surely held in the nonwoven fabric sheet 6, it is desirable that the hydrophobic synthetic fibers 11 therein are long in some degree and that the nonwoven fabric sheet 6 has a sheet structure in which the hydrophilic fiber aggregates 12 can be readily secured on the surfaces of the hydrophobic synthetic fibers 11. For example, in a point-bonded nonwoven fabric of heat-fusible short fibers, the hydrophilic fiber aggregates 12 could not be surely held among the hydrophobic synthetic fibers 11 and will readily drop off. Therefore, as so mentioned above, such a thermal-bonded nonwoven fabric produced in a through-air bonding process is preferred for the leakage-preventing side walls. Alternatively, the thermal-bonded nonwoven fabric may be heated with a heat roller instead of hot air. A spun-bonded nonwoven fabric of heat-fusible filaments is also usable for leakage-preventing side walls.

The basis weight of the nonwoven fabric sheet 6 preferably falls between 20 and 60 g/m$^2$, and the thickness (bulkiness) of the nonwoven fabric sheet 6 preferably falls between 0.3 and 10 mm, more preferably between 0.3 and 2 mm. In case where the basis weight and the thickness of the nonwoven fabric sheet 6 are defined to fall within the ranges as above, when the leakage-preventing side walls 5 made of the nonwoven fabric sheet 6 are brought into contact with the skin of a wearer, they hardly give a rigid feel, and, in addition, when a small amount of liquid or sweat is given to the surface of the leakage-preventing side walls 5, it can smoothly pass through the space between hydrophobic synthetic fibers 11 owing to the liquid absorbency of the hydrophilic fiber aggregates 12.

In order that such a small amount of liquid given to the side walls can be readily absorbed by the hydrophilic fiber aggregates 12, it is desirable that the hydrophilic fiber aggregates 12 are suitably dispersed among the hydrophobic synthetic fibers 11. Also preferably, the nonwoven fabric sheet 6 contains from 70 to 98% by weight of the hydrophobic synthetic fibers 11 and from 2 to 30% by weight of the hydrophilic fibers 12*a*, some in the form of the aggregates 12 and others in the non-aggregated form. More preferably, the hydrophilic fibers 12*a* account for from 2 to 10% by weight of the nonwoven fabric sheet 6. If the hydrophobic synthetic fibers 11 and the hydrophilic fibers 12*a* are blended within the defined range, the leakage-preventing side walls 5 formed from the nonwoven fabric sheet 6 are well resistant to liquid permeation even when a large amount of liquid is given thereto, and are therefore effective for preventing the liquid from leaking in the width direction. In addition, they can readily absorb a small amount of liquid given thereto, owing to the hydrophilic fiber aggregates 12 dispersed therein.

The hydrophilic fiber aggregates 12 may be uniformly distributed throughout the nonwoven fabric sheet 6 from its face to back, but it is desirable that the hydrophilic fiber aggregates 12 do not appear on the surface of the first and second portions 5A, 5B of the leakage-preventing side walls 5, 5. Concretely, when the nonwoven fabric sheet 6 comprises a layer 6*a* and a layer 6*b* in section with respect to the thickness thereof and when the nonwoven fabric sheet 6 is so folded that the layer 6*a* is exposed outside of the side wall 5 and the layer 6*b* is inside of the side wall 5, it is desirable that the hydrophilic fiber aggregates 12 are not in the outer layer 6*a* but are dispersed only in the inner layer 6*b*, as in the embodiment shown in FIG. 9.

If the hydrophilic fiber aggregates 12 are in the outer layer 6*a*, the surface strength of the nonwoven fabric sheet 6 is lowered in the first and second portions 5A, 5B of the leakage-preventing side walls 5, 5, and, in addition, the hydrophilic fiber aggregates 12 may drop off toward the wearer's skin. If so, moreover, there is the possibility that a small amount of liquid retained by the hydrophilic fiber aggregates 12 will return to the first and second portions 5A, 5B to give a wet feel the wearer's skin.

Preferably, the outer layer 6*a* is as thin as possible, since the distance between the surface of the first and second portions 5A, 5B of the leakage-preventing side walls 5, 5 and the hydrophilic fiber aggregates 12 therein can be shortened and therefore a small amount of liquid on the surface of the first and second portions 5A, SB can be readily attracted by the aggregates 12. For this, it is desirable that the basis weight of the outer layer 6*a* is smaller than that of the inner layer 6*b*. Concretely, the basis weight of the outer layer 6*a* preferably falls between 5 and 15 g/m$^2$. Also preferably, the basis weight of the outer layer 6*a* is at most ⅓ of the overall basis weight of the nonwoven fabric sheet 6.

When menses are given to the topsheet 4 of the sanitary napkin 1, they pass through the topsheet 4 and are absorbed by the absorbent core 3. In case where such a large amount of liquid is given to the topsheet 4 and it flows in the width direction (X-direction) of the sanitary napkin 1, its flow is blocked by the leakage-preventing side walls 5, 5. This is because the nonwoven fabric sheet 6 that forms the leakage-preventing side walls 5, 5 comprises mainly the hydrophobic synthetic fibers 11 and is therefore highly resistant to liquid permeation. Therefore, the liquid having been given to the first portion 5A and the second portion 5B of the leakage-preventing side walls 5, 5 permeates little in the leakage-preventing side walls 5, 5, and most of it is returned to the topsheet 4 and is then absorbed by the absorbent core 3.

At this time, however, a small amount of menses will often remain on the first and second portions 5A, 5B. In the invention, the liquid thus remaining is readily attracted and absorbed by the hydrophilic fiber aggregates 12 which have a high density and are dispersed in the nonwoven fabric sheet 6. In addition, sweat having adhered to the first and second portions 5A, 5B or its vapor is also readily absorbed by the aggregates 12. As a result, little liquid and vapor remain between the first and second portions 5A, 5B and the wearer's skin, and the side walls do not give a wet feel to a wearer.

Figure 4:
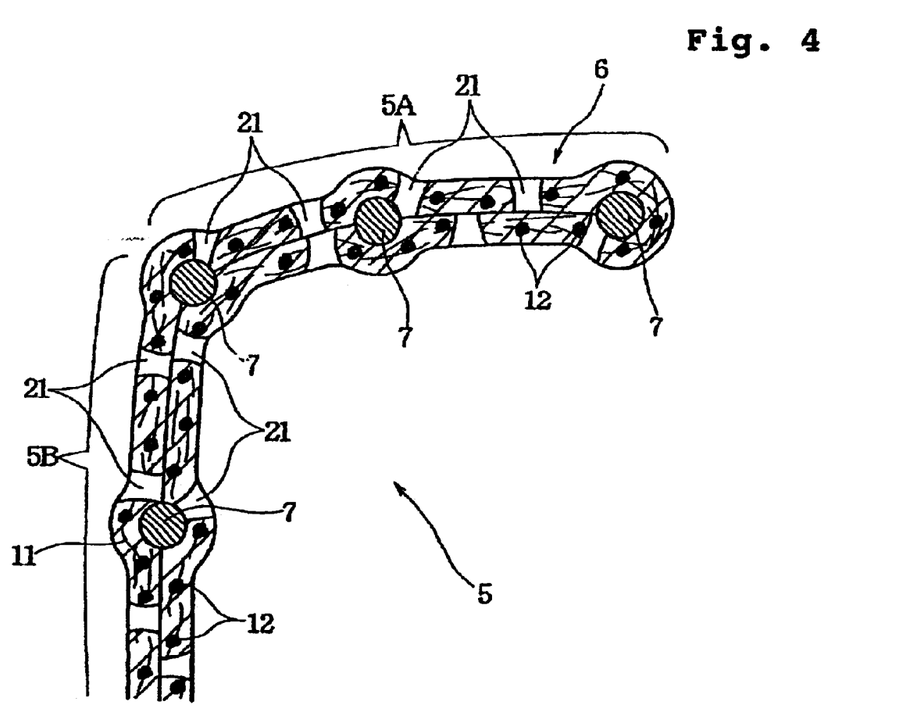
FIG. 4 is an enlarged cross-sectional view of a portion of another embodiment of the leakage-preventing side wall.

As shown in FIG. 11, the nonwoven fabric sheet 6 may be needled to form a large number of apertures 21 therein, and the nonwoven fabric sheet 6 thus having the apertures 21 may be formed into the leakage-preventing side walls 5, 5. FIG. 4 shows a cross-sectional view of the leakage-preventing side walls 5, 5 that are formed from the nonwoven fabric sheet 6 having such apertures 21 therein. In the embodiment illustrated in which the nonwoven fabric sheet 6 has the apertures 21, when a small amount of liquid or sweat has adhered to the first and second portions 5A, 5B of the side walls 5, 5, it enters the apertures 21 and is readily absorbed by hydrophilic fiber aggregates 12 adjacent to the inner surface of the apertures 21, and, as a result, little liquid remains on the surface of the first and second portions 5A, 5B of the side walls 5, 5.

If the diameter of each aperture 21 is too large, when a large amount of liquid is given to the side walls 5, 5, it will excessively pass through the apertures 12 to thereby lower the resistance of the leakage-preventing side walls 5, 5 to liquid permeation. Therefore, the diameter of each aperture 21 preferably falls between 0.3 and 2.0 mm, and the area occupied by all the apertures 21 preferably falls between 5 and 60% of the surface area of the nonwoven fabric sheet 6.

Figure 5:
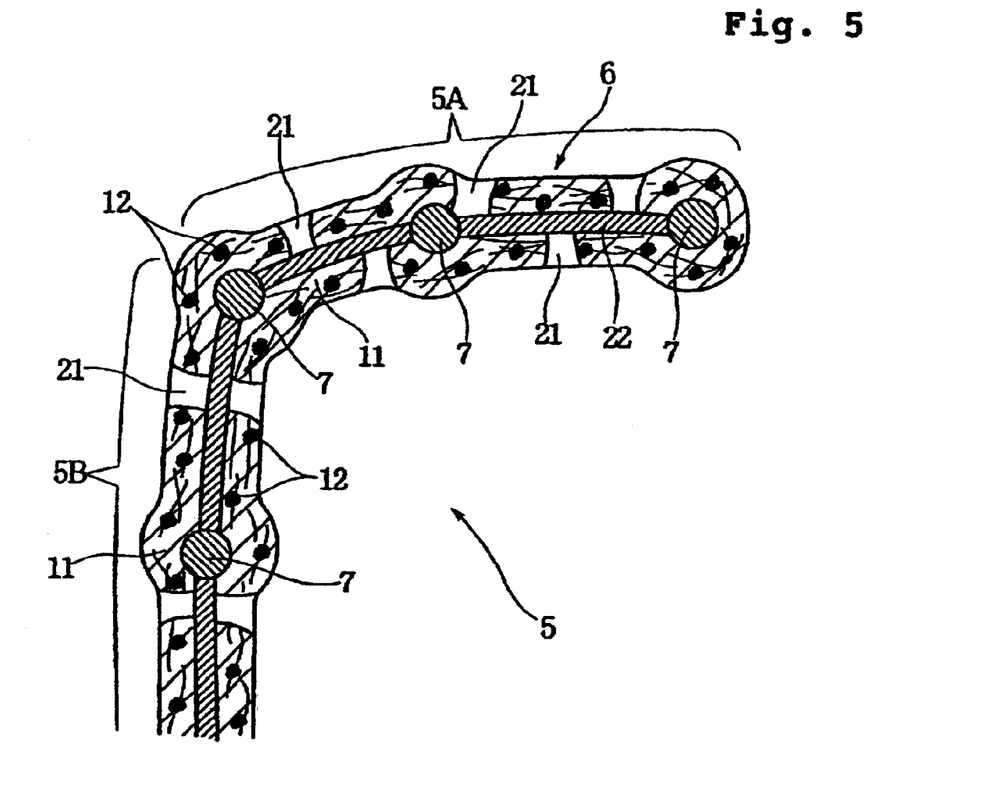
FIG. 5 is an enlarged cross-sectional view of a portion of still another embodiment of the leakage-preventing side wall.

As shown in FIG. 5, the leakage-preventing side walls 5, 5 may be so constructed that a thin liquid-absorbent layer 22 is disposed between the confronting faces of the thus-folded nonwoven fabric sheet 6. The liquid-absorbent layer 22 may be made of thin paper, air-laid pulp, a SAP sheet, a spun-laced nonwoven fabric of rayon, a melt-blown nonwoven fabric of synthetic fibers processed to be hydrophilic, a pulp sheet, or any other suitable materials comprising hydrophilic fibers or fibers processed to be hydrophilic.

In case where the liquid-absorbent layer 22 is disposed inside the side walls, the nonwoven fabric sheet 6 is preferably formed with a large number of apertures 21. In the embodiment of the leakage-preventing side walls 5, 5 of FIG. 5, the liquid having adhered to the first and second portions 5A, 5B of the side walls passes through the apertures 21 and is then absorbed by the liquid-absorbent layer 22, and a small amount of liquid or sweat still remaining on the first and second portions 5A, SB is absorbed by the aggregates 12. In this, therefore, little liquid remains on the surface of the first and second portions 5A, 5B of the side walls.

The ability of the liquid-absorbent layer 22 to readily absorb the liquid having remained on the surface of the leakage-preventing side walls 5, 5 is preferably as follows: A sample of the liquid-absorbent layer 22 is dipped in a physiological saline solution for 1 minute, and then left on metal gauze for 3 minutes to dewater it. In that condition, the saturated absorption per unit area (1 cm$^2$) of the thus-wetted sample is preferably at least 2 times, more preferably from 2 to 20 times the weight per the unit area of the dry sample.

When the liquid-absorbent layer 22 is disposed, the leakage-preventing side walls 5, 5 become highly stiff and will readily rise from the surface of the sanitary napkin 1. However, if too stiff, they will give a rigid feel to the skin of a wearer. Therefore, the stiffness of the liquid-absorbent layer 22 in the longitudinal direction (Y-direction) is preferably at most 50 mm, measured in a cantilever method according to JIS (Japanese Industrial Standard)-L-1096-6.19.1. In JIS-L1096-6.19.1, a sample of 2 cm×about 15 cm is cut out. The sample is placed on a horizontal table having a smooth surface and a 45-degree slope at one end thereof while aligning the shorter side of the sample on a basic line of a scale. Then, the sample is slowly slid toward the slope by an appropriate manner. When one end of the sample comes into contact at the center thereof with the slope, the position of the other end of the sample is read by the scale. Stiffness (bending resistance) is expressed by the migration length (mm) of the sample.

The liquid-absorbent layer 22 may be disposed throughout the entire region of the interiors of the leakage-preventing side walls 5, 5. Preferably, however, it is disposed only in the second portion 5B of each side wall, but not in the first portion 5A thereof.

Figure 6:
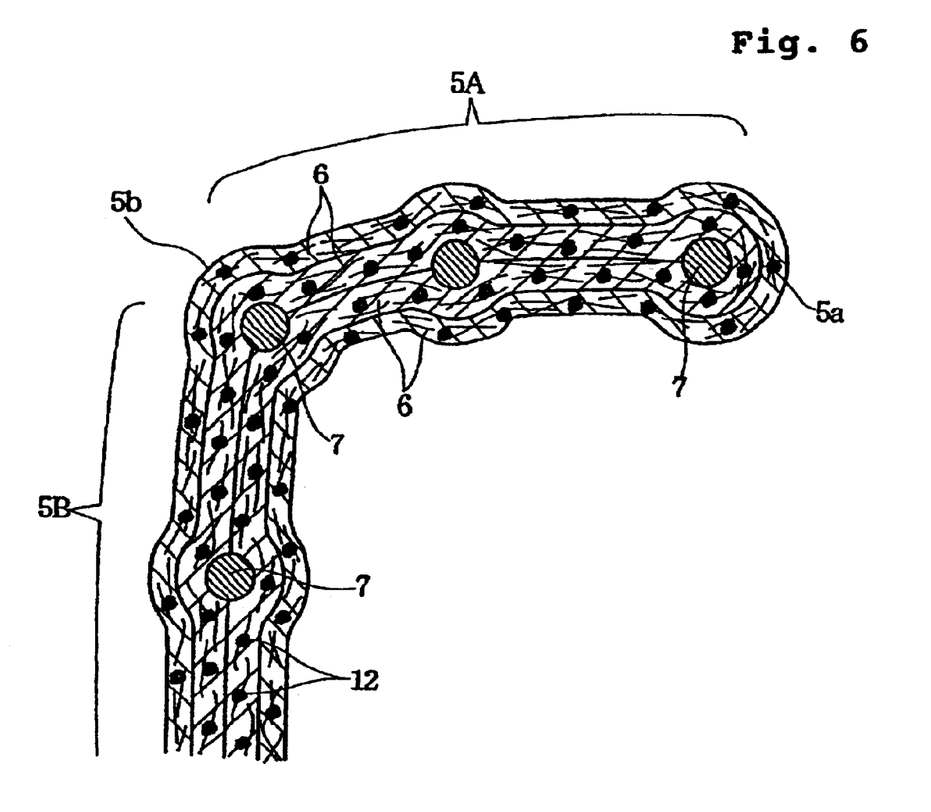
FIG. 6 is an enlarged cross-sectional view of a portion of still another embodiment of the leakage-preventing side wall.

As shown in FIG. 6, the leakage-preventing side walls 5, 5 may be so constructed that the nonwoven fabric sheet 6 having been folded into two is further folded into two at the top of the side wall, and therefore the thus-constructed side wall has a four-layer structure. In this construction, the number of the aggregates 12 to be in the leakage-preventing side walls 5, 5 can be increased, and therefore the overall ability of the aggregates 12 to absorb a small amount of liquid or sweat having adhered to the first and second portions 5A, 5B of each side wall is thereby enhanced.

Figure 7:
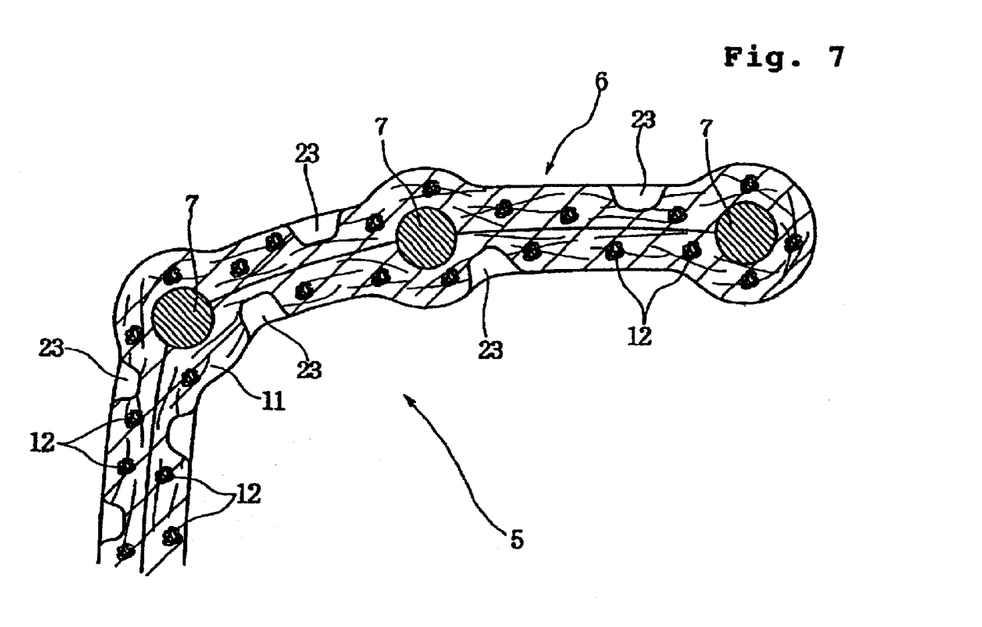
FIG. 7 is an enlarged cross-sectional view of a portion of still another embodiment of the leakage-preventing side wall.

FIG. 7 is a cross-sectional view showing still another embodiment of the leakage-preventing side walls 5, 5.

The nonwoven fabric sheet 6 to form the leakage-preventing side walls 5, 5 of this embodiment is specifically so processed as to have a large number of recesses 23 each caving in from the outer surface of the side walls 5 toward the inside thereof. For forming the recesses 23, for example, the nonwoven fabric sheet 6 may be pressed from its one surface, which is to be exposed outside of the side walls 5, with an embossing roll. The depth of each recess 23 may fall between 0.1 and 1 mm or so, and the area occupied by all the recesses 23 may fall between 3 and 30% of the surface area of the nonwoven fabric sheet 6.

In the nonwoven fabric sheet 6 for this embodiment, the fiber density of the portions processed to form the recesses 23 is increased. In this embodiment, therefore, when a small amount of liquid has remained on the first and second portions 5A, 5B, the bottom of each recess 23 having such an increased density draws the liquid owing to the capillary action, and the thus-drawn liquid is then absorbed by aggregates 12 existing adjacent to the recesses 23. Accordingly, the side walls of this embodiment are more effective for preventing the occurrence of residual liquid on their surface.

Figure 8:
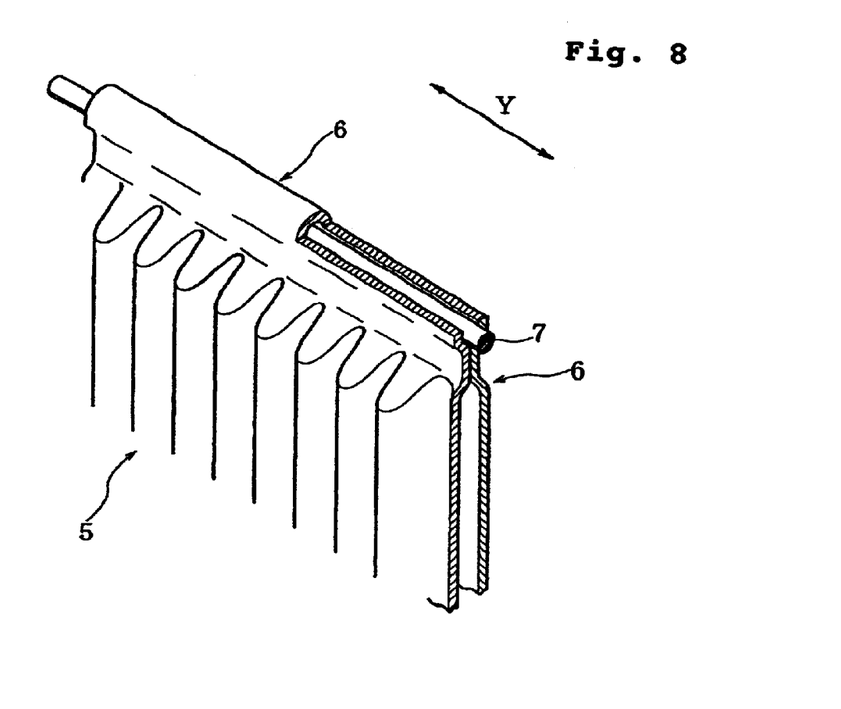
FIG. 8 is an enlarged cross-sectional view of a portion of still another embodiment of the leakage-preventing side wall.

FIG. 8 is a partially-cut perspective view showing still another embodiment of the leakage-preventing side walls 5, 5.

As has been described above, the leakage-preventing side walls 5, 5 of this embodiment are also formed from the nonwoven fabric sheet 6 that comprises the hydrophobic synthetic fibers 11 and the hydrophilic fiber aggregates 12. For these side walls 5, 5, the nonwoven fabric sheet 6 is specifically so corrugated that the hills and the valleys are alternated in the longitudinal direction (Y-direction). This corrugation can be formed by pressing the nonwoven fabric sheet 6 between rolls having corrugated surfaces. In the thus-corrugated nonwoven fabric sheet 6, the fiber density of the top of each hill and the fiber density of the bottom of each valley are higher than the fiber density of the other portions. In the leakage-preventing side walls 5, 5 made of the thus-corrugated nonwoven fabric sheet 6, therefore, a small amount of liquid can be readily led to the aggregates 12 existing in these portions having an increased fiber density.

FIG. 12 shows one example of a method for producing the nonwoven fabric sheet 6 shown in FIG. 9.

In the production method of FIG. 12, hydrophobic synthetic fibers 11 having a length of from 38 to 64 mm are fed into the first-stage carding unit 31, and are carded and opened by the pins 33 of the rotary roll therein. The hydrophobic synthetic fibers 11 are satisfactorily long, relative to the pitch of the pins 33 in the circumferential direction of the roll, and are therefore aligned in the machine direction (MD) to form a fibrous web, which is to be the outer layer 6a of the side walls 5, 5.

On the other hand, hydrophobic synthetic fibers 11 having a length of from 38 to 64 mm and hydrophilic fibers 12a (of cotton) having a length of from 5 to 25 mm are fed into the second-stage carding unit 32, and are carded and opened by the pins 34 of the rotary roll therein. The hydrophobic synthetic fibers 11 are satisfactorily long and stiff, and are therefore aligned in MD owing to the opening force of the pins 34. However, the hydrophilic fibers 12a are short and those of cotton or the like are not stiff but soft. Therefore, when they have received the opening force of the pins 34, they are not aligned in MD and most of them are massed or crimped to form aggregates 12, which are held between the pins 34. As a result, in the fibrous web thus formed in the second stage, the hydrophilic fiber aggregates 12 are dispersed among the hydrophobic synthetic fibers 11 aligned in MD. The fibrous web formed in the second stage is to be the inner layer 6b of the side walls 5, 5.

The two fibrous webs formed in the first and second stages are stacked and then conveyed to a through-air system heating chamber 35, in which the hydrophobic synthetic fibers 11 in the fibrous webs are thermally bonded to one another and the hydrophilic fiber aggregates 12 therein are fixed on the fused surfaces of the hydrophobic synthetic fibers 11. Through the process, the intended nonwoven fabric sheet 6 as illustrated is produced.

In place of the heating chamber 35, a hot roll may be used for thermally bonding the hydrophobic synthetic fibers 11 in the fibrous webs.

Of course, the nonwoven fabric sheet 6 should not be limited to such a two-layer structure. For example, the nonwoven fabric sheet 6 may be formed into a single-layer structure by using only the second-stage carding unit 32 shown in FIG. 12. In this case, the hydrophilic fiber aggregates 12 are uniformly dispersed among hydrophobic synthetic fibers 11 throughout the nonwoven fabric sheet 6.

As described in detail hereinabove with reference to its preferred embodiments, the leakage-preventing side walls in the absorbent article of the invention can readily absorb a small amount of liquid or sweat having adhered thereto. Therefore, the surfaces of the leakage-preventing side walls are not wettish and do not give a stuffy feel to a wearer.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent article comprising a topsheet, a backsheet and an absorbent core positioned between the topsheet and the backsheet, and having leakage-preventing side walls on a liquid-receiving side of the article, the leakage-preventing side walls extending in a longitudinal direction of the article and lying opposite one another in a width direction of the article, wherein
   at least a liquid-receiving face of each leakage-preventing side wall is made of a fibrous sheet that contains hydrophobic fibers thermally bonded to one another and hydrophilic fibers shorter than the hydrophobic fibers, and at least a part of the hydrophilic fibers form aggregates which are dispersed in the fibrous sheet and are bonded to the hydrophobic fibers.

2. The absorbent article as set forth in claim 1, wherein the hydrophilic fiber aggregates are, when the fibrous sheet comprises an outer layer and an inner layer in section with respect to the thickness thereof, not in the outer layer but are only in the inner layer.

3. The absorbent article as set forth in claim 2, wherein the basis weight of the fibrous sheet falls between 20 and 60 $g/m^2$, and the basis weight of the outer layer of the fibrous sheet falls between 5 and 15 $g/m^2$.

4. The absorbent article as set forth in claim 1, wherein the fibrous sheet has a plurality of apertures formed therein.

5. The absorbent article as set forth in claim 1, wherein the fibrous sheet is folded back at the top of the side wall, and a liquid-absorbent layer is disposed between the confronting faces of the thus-folded fibrous sheet.

6. The absorbent article as set forth in claim 1, wherein the fiber density of the hydrophilic fiber aggregates is higher than the fiber density of a portion of the fibrous sheet not containing the aggregates therein.

7. The absorbent article as set forth in claim 6, wherein the fiber density of the hydrophilic fiber aggregates falls between 1.5 and 3 times the fiber density of the portion of the fibrous sheet not containing the aggregates therein.

8. The absorbent article as set forth in claim 1, wherein the hydrophobic fibers have a length of from 38 to 64 mm, and the hydrophilic fibers have a length of from 5 to 25 mm.

9. The absorbent article as set forth in claim 1, wherein the fibrous sheet contains from 70 to 98% by weight of hydrophobic fibers and from 2 to 30% by weight of hydrophilic fibers.

* * * * *